United States Patent
Hearn et al.

(10) Patent No.: US 11,480,026 B2
(45) Date of Patent: Oct. 25, 2022

(54) NANO-THERMITE WELL PLUG

(71) Applicant: ConocoPhillips Company, Houston, TX (US)

(72) Inventors: David D. Hearn, Houston, TX (US); Casey Hirschmann, Houston, TX (US); Randall S. Shafer, Houston, TX (US)

(73) Assignee: CONOCOPHILLIS COMPANY, Houston, TX (US)

(*) Notice: Subject to any disclaimer, the term of this patent is extended or adjusted under 35 U.S.C. 154(b) by 0 days.

(21) Appl. No.: 17/075,897

(22) Filed: Oct. 21, 2020

(65) Prior Publication Data

US 2021/0087904 A1   Mar. 25, 2021

Related U.S. Application Data

(62) Division of application No. 15/705,513, filed on Sep. 15, 2017, now Pat. No. 10,871,050.

(60) Provisional application No. 62/402,810, filed on Sep. 30, 2016.

(51) Int. Cl.

| | | |
|---|---|---|
| *E21B 33/13* | (2006.01) | |
| *E21B 47/06* | (2012.01) | |
| *E21B 36/00* | (2006.01) | |

(52) U.S. Cl.
CPC .............. *E21B 33/13* (2013.01); *E21B 36/00* (2013.01); *E21B 47/06* (2013.01)

(58) Field of Classification Search
CPC ........ E21B 29/02; E21B 23/06; E21B 31/002; E21B 33/13; E21B 33/12; E21B 33/134; E21B 36/008

See application file for complete search history.

(56) References Cited

U.S. PATENT DOCUMENTS

| | | |
|---|---|---|
| 3,830,299 A | 8/1974 | Thomeer |
| 6,474,414 B1 | 11/2002 | Gonzalez et al. |
| 6,478,088 B1 | 11/2002 | Hansen et al. |
| 6,664,522 B2 | 12/2003 | Spencer |
| 6,828,531 B2 | 12/2004 | Spencer |

(Continued)

FOREIGN PATENT DOCUMENTS

| | | |
|---|---|---|
| WO | 2011151271 A1 | 12/2011 |
| WO | 2013135583 A2 | 9/2013 |

(Continued)

OTHER PUBLICATIONS

Piercey, D. G.; Klapotke, M. Nanoscale Aluminum-metal oxide (thermite) reactions for application in energetic materials. Central European Journal of Energetics Materials, 2010, 7(2), 115-129.

(Continued)

*Primary Examiner* — Zakiya W Bates
(74) *Attorney, Agent, or Firm* — Boulware & Valoir

(57) ABSTRACT

A composition and methods for setting a plug for well bores undergoing plugging and abandonment operations is described. Methods of setting the plug are also described include placing a blocking device below the plug location and creating a void space above the blocking device; placing a heat resistant base plate above the blocking device and introducing nano-thermite clusters and expandable bismuth alloy pellets into the void space; igniting the thermite and cooling the melted alloy to form a permanent plug in the void space.

6 Claims, 5 Drawing Sheets

(56) References Cited

U.S. PATENT DOCUMENTS

| | | |
|---|---|---|
| 7,152,657 B2 | 12/2006 | Bosma et al. |
| 7,290,609 B2 | 11/2007 | Wardlaw et al. |
| 2005/0109511 A1 | 5/2005 | Spencer |
| 2006/0144591 A1 | 7/2006 | Gonzalez et al. |
| 2007/0137826 A1 | 6/2007 | Bosma et al. |
| 2008/0028922 A1 | 2/2008 | Wilson et al. |
| 2009/0301337 A1* | 12/2009 | Wilson .................. F42B 12/06 102/517 |
| 2011/0167795 A1* | 7/2011 | Gangopadhyay ......... F02K 9/08 60/254 |
| 2011/0220357 A1 | 9/2011 | Segura et al. |
| 2015/0034317 A1 | 2/2015 | Skjold |
| 2015/0034341 A1 | 2/2015 | Pigeon |
| 2015/0211322 A1 | 7/2015 | Lowry et al. |
| 2015/0211326 A1 | 7/2015 | Lowry et al. |
| 2015/0211327 A1 | 7/2015 | Lowry et al. |
| 2015/0211328 A1 | 7/2015 | Lowry et al. |
| 2015/0343417 A1 | 12/2015 | Puranik et al. |
| 2015/0368542 A1 | 12/2015 | Carragher |
| 2016/0090812 A1* | 3/2016 | Zhao .................. E21B 36/00 264/319 |
| 2017/0145782 A1 | 5/2017 | Ferg |

FOREIGN PATENT DOCUMENTS

| | | |
|---|---|---|
| WO | 2014096858 A2 | 6/2014 |
| WO | 2015116261 A1 | 8/2015 |

OTHER PUBLICATIONS

Puszynski, J. A.; Swiatkiewicz, J. J.; Higa, K. Processing of aluminum-based nanothermites in a circulating mixer. Presentation in the 44th Annual Armament Systems: Gun & Missile Systems Conf. & Exhibition, (Apr. 2009).

Puszynski, J. A.; Bulian, C. J.; Swiatkiewicz, J. J. Ignition characteristics of nanothermite systems. International Journal of Energetic Materials and Chemical Propulsion, 2008, 7, 73-86.

International Search Report Mailed in PCT Application No. PCT/US2017/051745 dated Nov. 20, 2017, 7 Pages.

\* cited by examiner

NANO-THERMITE WELL PLUG

PRIOR RELATED APPLICATIONS

This application is a Divisional application of U.S. application Ser. No. 15/705,513, filed Sep. 15, 2017, entitled "Nano-thermite Well Plug", which is a non-provisional application that claims benefit under 35 USC § 119(e) to U.S. Provisional Application Ser. No. 62/402,810, filed Sep. 30, 2016, entitled "Nano-thermite Well Plug." Each of these applications is incorporated herein in their entirety for all purposes.

FEDERALLY SPONSORED RESEARCH STATEMENT

Not applicable.

REFERENCE TO MICROFICHE APPENDIX

Not applicable.

FIELD OF TIE DISCLOSURE

The disclosure relates generally to methods and materials for plugging and abandoning well operations and specifically to the use of nano-thermite materials and methods of use.

BACKGROUND OF THE DISCLOSURE

There are several thousand active oil and gas wells located around the world, with thousands more to come on-stream in the next ten years. The wells differ in design, size, cost and economic benefit. The wellbores have one thing in common: sooner or later they will be decommissioned and abandoned.

The decision to plug and abandon (P&A) a well or field is invariably based on economics. Once production delivers less than the operating expenses, it is time to consider abandonment. In some situations, the decision is made with the knowledge that considerable reserves remain, but the cost to extract these resources is more than the projected income.

There are typically regulatory requirements associated with the P&A process to ensure that strata, particularly freshwater aquifers, are adequately isolated. The plug's length, cross-section, position and verification tests are regulated and depend on the type and location of the well being plugged. Thus, cost to P&A a well can vary by many millions of dollars depending on location, and whether the well is offshore or onshore. Minimizing costs, without sacrificing well integrity, is critical to operators, who make a significant investment with no financial return in the case of P&A operations.

FIG. 1 displays a simple schematic of a basic plug. A modern requirement for a permanent well barrier is that it must include all annuli, extending to the full cross section of the well and seal both vertically and horizontally. In FIG. 1, a cement plug is sealing vertically inside the casing and sealing both horizontally and vertically in the casing-formation annulus above the casing shoe. However, cement is easily contaminated with mud, which results in placement issues and often resulting in plug failure.

Although cement is the most common plug material, wellbores have also been plugged with metal seals or plugs that are melted and then solidified in place. For instance, eutectic metals are heated until molten and then the molten eutectic metal is introduced into confined regions of downhole structures requiring fluid sealing. However, such plugs required substantial amounts of electrical power to heat the metals, thus there is a need for power generating units, long, heavy electrical cables, and significant excess electrical capacity, particularly on off-shore structures where weight and space are at a premium.

As such, improvements in plug composition and methods are desired to save money. One alternative is to "cast-in-place" a metal plug. An alloy, such as an expandable bismuth alloy, is heated in place to form a liquid that easily penetrates small crevices and cracks, and hardens in place forming a tight plug. A heater tool is commercially available from BiSN Oil Tools, and described in WO2011151271 and WO2014096858 and can heat such cast-in place bismuth alloy plugs. The BiSN Wel-lok M2M Bridge Plug™ can run on standard wireline, slick line or coil tubing. It uses a bismuth-based alloy that is melted in situ using a chemical reaction heater that uses materials, such as thermite, to generate heat. However, this tool can only heat a small volume of alloy at a time and thus other methods and tools are still needed for P&A.

Thermite is normally known as a pyrotechnic composition of a metal powder and a metal oxide. The metal powder and the metal oxide produce an exothermic oxidation-reduction reaction known as a thermite reaction. A number of metals can be the reducing agent, e.g. aluminum. If aluminum is the reducing agent, the reaction is called an aluminothermic reaction. Most of the varieties are not explosive, but may create short bursts of extremely high temperatures focused on a very small area for a short period of time. The temperatures may reach as high as 3000° C.

At such a high temperature, the thermite plug and wellbore casings melt and form a seal. However, igniting the reaction is problematic, especially for P&A operations, because of the regulated plug characteristics. Cement plugs are typically required to be 50 or more meters in length, and even alloy plug may require significant length under older regulations. However, the size of the ignitor, the diameter of the wellbore and the length of the plug will limit the volume of thermite, which can result in an incomplete plug. Further, for longer and wider plugs, each cluster, canister, or pod of thermite must have its own ignitor. As thermite is typically in the form of coarse particles, it is slow to burn and requires higher temperature to start reacting. Thus, cost can quickly add up just for the ignition step.

As such, there exists a need to improve plug formation in P&A operations while also decreasing cost and time. In particular, a method that avoids costly rig use would be desired, especially for offshore P&A where a rig can cost a half a million dollars a day.

SUMMARY OF THE DISCLOSURE

Described herein is a nanoscale energetic composition (also called metastable intermolecular composites or MIC) for plugging an oil well during plugging and abandonment (P&A) operations and method of use. Specifically, a nano-thermite composition, preferably comprising aluminum and another metal such as bismuth, is utilized as a well plug material and for melting wells, especially those with small diameter. A commonly used heater ignites the nano-thermite reaction and the resulting exothermic reaction melts the metal plug material, metal tubing and casing to form a seal across a wellbore.

Nano-thermites exhibit vastly differing characteristics compared to their well-known micro or larger scale counterparts, and have certain advantages, especially in oil and gas applications.

Conventional thermite for well plugging is described in US201500343417. The conventional thermite is limited because of the size requirements of permanent well plugs and the thermite's ignition and temperature requirements. For large plugs, an ignition substance such as magnesium is needed for each cluster/canister/pod of conventional thermite utilized. Magnesium is a difficult material to handle and can spontaneous combustion or prematurely ignite in the wellbore.

In contrast, the nano-thermite used in the present methods utilizes much smaller particles than conventional thermite. The reaction rate of a nanoscale thermite is several orders of magnitude larger than thermites in micron scale and the much larger surface area of nanoparticles can significantly change combustion behavior, as well as ignition behavior by increasing sensitivity. This results in lower ignition temperatures being needed for nano-thermites. A nano-bismuth thermite, for example, has an ignition temperature that is about 50% less than conventional bismuth thermite. This is beneficial in wellbores because heaters commonly used in oil and gas applications can be utilized to ignite the thermite reaction. Thus, there will be a reduction in the cost of ignitors and number of heating elements that are typically needed with conventional thermite.

Additionally, the lower ignition temperatures facilitate ignition of clusters of thermite. The clusters can then be any shape or a collection of different shapes within the well, depending on the application. Further, nano-thermite has been shown to have the same heat value per volume (not mass) as conventional thermite, making it a suitable replacement for forming plugs. Additionally, the faster reaction rate can minimize heat losses. Thus, the use of nanoparticles allows for better controlled reactions and lower thermite temperatures. Thus, the reaction can be optimized for each well.

Nano-thermites also exhibit an optimal reactivity that correlates with gas production instead of temperature. This rapid gas evolution will increase pressure and the rate of burning, which mean there is a greater heat transfer to the surface, i.e. wellbore and casings. As such, the produced gas will assist in melting the wells for the metal plug. Thus, smaller amounts of nano-thermites can be utilized to achieve the same amount of melting as the larger thermite. Explosive force from the thermite reaction can also cause the tubulars to fail, which will result in the metal and thermite reactive products combining to form the plug.

MICs such as nano-thermites are also useful where the amount of reactants or reaction space is limited. The nano-thermites can form clusters, each of having a unique shape or size. The differently shaped clusters can then be dropped or placed in the well or be placed in a heater made of steel or other material. The clusters can then be ignited together or individually. In contrast, conventional thermite in the same size clusters or shapes would not ignite due to higher ignition temperature.

It is expected that the disclosed materials and methods will reduce the cost of P&A operations because a workover or drilling rig will not be required, complex ignition systems normally used with conventional thermite are not needed, and the amount of nano-thermite can be tuned to create a plug with the exact specifications for the wellbore being plugged. Specifically, P&A operations can be performed through the tubing, utilizing wireline or coil tubing. The production tubing also does not have to be pulled to set the plug, saving time and money. A "through-tubing" P&A is particular beneficial offshore because it avoids expensive rig time, a tremendous benefit where an offshore rig can cost a half million per day.

Although the method is described as a "through tubing" method, the tubing is in fact actually removed (wholly or partially) at the section to be plugged. Nevertheless, it is appropriately designated through tubing, because the entirety of the tubing need not be pulled out of the well prior to the P&A operation. The method describes a variety of ways to remove a short region of tubing and/or casing and access the plugging interval.

Nano-thermite has a similar composition to conventional thermite but utilizes smaller particles in the nanometer range. Aluminum is a primary component of inorganic energetic compositions and has undergone extensive investigations for formulating propellants, explosives and thermites. In the present methods, it is used as the fuel, along with one or more metal oxides to reduce the nano-aluminum in an oxidation/reduction ("redox") reaction.

One consideration when using nano-aluminum is the outer passivation of the metal surface. In conventional thermite, the outer layer of alumina is negligible. In the nanoscale, the outer layer becomes a significant portion of the mass of the aluminum nanoparticles. Further, the difference in melting temperature of aluminum and is alumina is large. The melting temperature of aluminum is around 660° C., which is well below the melting temperature of aluminum oxide (2072° C.), making it complicated to determine what exactly happens while heating the nanoparticles. However, research has shown that the nano-thermites are, unexpectedly, capable of igniting closer to the aluminum melting point. Thus, the smaller particles are able to interact more efficiently, resulting in a quicker reaction that is ignited at a lower temperature, in spite of the alumina layer.

The basic nano-thermite reaction is given in Equation 1 and Table 1 displays some of the common nano-thermite compositions and ignition temperatures.

$$M_xO_y + Al \rightarrow M + Al_2O_3, \text{ wherein } M = \text{metal} \qquad \text{Equation 1:}$$

TABLE 1

Characteristics of common Nano-thermite reactions

| Thermite reaction | Q [cal/g] | Q [cal/cm3] | Gas generation 1 atm, [g gas/ g mixture] | Tad [K] | ESD ignition energy (mJ) | Ignition Temperature K Nano |
|---|---|---|---|---|---|---|
| 2Al + Fe2O3 -> 2Fe + Al2O3 | 945.4 | 3947 | 0.0784 | 3135 | 0.113 | 1400 |
| 2Al + Bi2O3 -> 2Bi + Al2O3 | 505.1 | 3638 | 0.894 | 3319 | 0.0001 | 850 |
| 2Al + MoO3 -> Mo + Al2O3 | 1124 | 4279 | 0.2473 | 3688 | 0.05 | 850 |
| 2Al + 3CuO -> 3Cu + Al2O3 | 974.1 | 4976 | 0.3431 | 2843 | | 1040 |

These compositions can be deposited into wells, included those with restricted or deviated tubing, to set one or more permanent plugs.

Bismuth is preferred in the nano-thermite material because bismuth expands 3.32% on solidification. Bismuth also has unusually low toxicity for a heavy metal. Such alloys have a higher density in liquid form than in their solid state and therefore expand upon solidification. However, any metal oxide normal used in thermites is acceptable.

The method can also employ expandable bismuth alloy pellets to contribute to plug formation. Exemplary bismuth alloys are described in U.S. Pat. No. 7,290,609. As a general rule, bismuth alloys of approximately 50% bismuth exhibit little change of volume (1%) during solidification. Alloys containing more than this tend to expand during solidification and those containing less tend to shrink during solidification. Additional alloys are described in US20150368542, which describes a bismuth alloy comprises bismuth and germanium and/or copper. Additional eutectic alloys to plug wells or repair existing plugs in wells are described in U.S. Pat. No. 7,152,657; US20060144591; U.S. Pat. Nos. 6,828, 531; 6,664,522; 6,474,414; and US20050109511. Eutectic alloys or other metals or alloys can be placed with the nano-thermite and in some cases used as an encapsulating material for the nano-thermite.

The nano-thermite clusters can be any shape, but, preferably are balls and rods. The thermite is molded and compressed to be on the order of 50-100 nm, preferable 50-80 nm, and most preferable 75 nm. This results in higher energy output. Molded and compressed clusters insure ignition and maximum volume. If left uncompressed, the clusters have limited energy available and will need higher energy so propagate ignition from cluster to cluster.

The clusters can then be encapsulated in a coating plastic, bismuth, other low melt material. This protects the thermite from any environmental contamination that might prevent ignition. The coating also protects the clusters when they are dropped or placed in the well bore and insulate the nano-thermite from prematurely ignition in the well or on the surface.

The coatings can be any thermoplastic such as acrylic, nylon, polycarbonates, resin, polyether sulfones/sulfates, polyetheretherketone, polystyrene, polypropylene, polyvinylchloride, polyphenylene oxide, and the like. Other low melt material such as fusible alloys containing lead, tin, cadmium, zinc, or mercury can also be used or other metals and alloys. Bismuth alloy is preferred for some applications because of its low toxicity and expansion on solidification. The coating material is designed to facilitate ignition of nano-thermite clusters.

Methods of using the nano-thermite to form plugs are also described. Generally, the method for forming a plug comprising nano-thermite, reservoir casing and optional additional plug material includes introducing a wide range setting plug at a predetermined location just under the desired plug location and creating a void area for the permanent plug just above the setting plug. Energetics can be used to create the void area for the permanent plug by rupturing and expanding the casing and tubing. Thus, there is no need to mill tubulars to gain access and any cement present will be fractured or pulverized, falling down hole. Alternatively, if the exterior cement is of good quality, a small section (<2 m) can be milled or cut. See e.g., COP 42399, U.S. Ser. No. 62/402,796, incorporated by reference herein in its entirety for all purposes.

A heat resistant base plate composed of ceramic material can then be placed above the setting plug to protect it from the thermite reaction. The nano-thermite material and any other material (such as bismuth alloy pellets) for the permanent plug can then be dropped into the void space. A heat source, such as a bailer, is then run into the nano-thermite material to initiate the thermite redox reaction. Once ignited, the heater is immediately removed to avoid deposition of material on the heater. The thermite reaction may produce enough heat to melt the metal tubing and casing, thus contributing to the permanent plug that stretches across the well bore to form a seal once the reactions ends and the melted material solidifies.

The setting plug serves to seal the well from above or below the melting position and void space, while the heat resistant base plate serves to protect the setting plug from the heat of the ignited heat generating mixture.

Primary and secondary plugs can be set in this way, and thereafter, the Christmas tree and BOP removed, and the well abandoned.

During the thermite reaction, liquid metal from the reacted nano-thermite material will flow out and ignite remaining unreacted thermite components. The heat of the reaction will melt low melt alloys, such as bismuth alloys, which will fill all void spaces, expanding on cooling to form a tight rock-to-rock plug. If needed, additional nano-thermite can be gravity fed from above to maximize the heat of the reaction and/or lengthen the plug. Thus, the reaction will be self-propagating from nano-thermite cluster to cluster.

Even if the base plug does not provide a perfect seal, the use of low melt bismuth alloys will quickly seal that base plug as the molten alloy front penetrates any gaps, and then cools and hardens. Any imperfections will thus quickly be sealed.

This summary is provided to introduce a selection of concepts that are further described below in the detailed description. This summary is not intended to identify key or essential features of the claimed subject matter, nor is it intended to be used as an aid in limiting the scope of the claimed subject matter.

As used herein, "thermite" refers to a composition of a metal fuel and metal oxide that undergoes an exothermic redox reaction when ignited by heat. This exothermic redox reaction is also called a "thermite reaction". If the metal fuel is aluminum, the exothermic redox reaction can also be called aluminothermic reaction.

As used herein, "conventional thermite" means thermite particles that are in the microscale or larger size range, e.g., >1 μm.

As used herein, "nano-thermite" means thermite particles in the nanoscale, e.g., <1 μm, preferably ≤500 nm, most preferred ≤200 nm in average diameter. This size limitation can include both the metal oxide and metal fuel.

As used herein, "clusters" refers to small chunks of material, but does not imply a particular shape. Clusters can thus be tetrapods, spheres, rod or disc-shaped, irregular, or any other shape. The key to the use of clusters is the ability to self-propagate ignition from one cluster to the next. In some embodiments, the clusters are molded and compressed to improve energy output and self-propagation.

As used herein, an "expandable" alloy is one that expands when cooled from the molten state by 1-3% or more.

As used herein, metal "pellets" refer to small pieces of metal in any shape that are small enough to be dropped into a well.

As used herein, a "P&A" refers to plug and abandon. Regulations require that the plugs be of sufficient quality to be "permanent," never allowing formation fluids to leak. However, it is recognized that even a permanently plugged and abandoned well may be reopened at a later time for various reasons. Therefore, "permanent" does not imply that the well will not be reopened, but instead refers to the quality of the plug—it needing the potential to last a long time.

As used herein, a "blocking device" is any device used to prevent cement or alloy from falling downhole, e.g., it provides a stable base on which to set a cast-in-place plug. This can be a mechanical device, such as basket, inflatable basket, plug, packer, cement plug on wireline, sand, etc. and the like.

The blocking device could also be a cement plug, barite plug, sand plug, resin plug, combinations thereof, a bolus of extra heavy mud, or any other non-mechanical blocking device. Since this only acts as a base for a permanent plug, it is not required to act as a permanent plug by itself, and the requirements are less stringent.

As used herein, "wide range setting plug" refers to a plug that can be set in wide range of hole diameters.

As used herein, "spud cone" bottom, e.g. on a heater or bailer, is conically shaped to allow penetration of material in the well when the device is lowered or dropped into the material.

"Tubular" or "tubing" can be used generically to refer any type of oilfield pipe, such as drill pipe, drill collars, pup joints, casing, production tubing and pipeline. However, generally we have referred to the inner tubing, such as injection tubing or production tubing as tubulars herein. The outer one or more tubing sets, we have referred to as "casing" herein.

As used herein, a "joint" is a length of pipe, usually referring to drill pipe, casing or tubing. While there are different standard lengths, the most common drill pipe joint length is around 30 ft [9 m]. For casing, the most common length of a joint is 40 ft [12 m].

As used herein, a "tubular string" or "tubing string" refers to a number of joints, connected end to end (one at a time) so as to reach down into a well, e.g., a tubing string lowers a sucker rod pump to the fluid level.

As used herein, a "Christmas tree" provides primary and back-up control facilities for normal production and wellbore shut-in. Christmas trees are found in a wide range of sizes and configurations, depending on the type and production characteristics of the well. The Christmas tree also incorporates facilities to enable safe access for well intervention operations, such as slick line, electric wireline or coiled tubing.

As used herein the "wellhead" refers to the surface termination of a wellbore that incorporates facilities for installing casing hangers during the well construction phase. The wellhead also incorporates a means of hanging the production tubing and installing the Christmas tree and surface flow-control facilities in preparation for the production phase of the well.

As used herein, a "blow out preventer" or "BOP" is a large device with a plurality of valves and fail-safes at the top of a well that may be closed if the drilling crew loses control of formation fluids. By closing the BOP (usually operated remotely via hydraulic actuators), the drilling crew usually regains control of the reservoir, and procedures can then be initiated to increase the mud density until it is possible to open the BOP and retain pressure control of the formation. BOPs come in a variety of styles, sizes and pressure ratings.

As used herein a "lubricator" is a long, high-pressure pipe fitted to the top of a wellhead or Christmas tree so that tools may be put into a high-pressure well. The top of the lubricator assembly includes a high-pressure grease-injection section and sealing elements. The lubricator is installed on top of the tree and tested, the tools placed in the lubricator and the lubricator pressurized to wellbore pressure. Then the top valves of the tree are opened to enable the tools to fall or be pumped into the wellbore under pressure. To remove the tools, the reverse process is used: the tools are pulled up into the lubricator under wellbore pressure, the tree valves are closed, the lubricator pressure is bled off, and then the lubricator may be opened to remove the tools.

As used herein "swarf" are the fine chips or coils of metal produced by milling the casing or tubing.

As used herein, a "cutter" is any downhole tube that can be used to cut casing or tubing, which is typically done when a tool is stuck, in order to retrieve the tubing string and send down fishing tools. There are a number of different types of such tools, some of which are named herein.

An "external cutter" is a type of cutter. The external cutter slips over the fish or tubing to be cut. Special hardened metal-cutters on the inside of the tool engage on the external surfaces of the fish. External cutters are generally used to remove the topmost, possibly damaged, portion of a fish to enable an overshot, or similar fishing tools, to engage on an undamaged surface.

As used herein, a "chemical cutter" is a type of cutter run on wireline to sever tubing at a predetermined point when the tubing string becomes stuck. When activated, the chemical cutter uses a small explosive charge to forcefully direct high-pressure jets of highly corrosive material in a circumferential pattern against the tubular wall. The nearly instantaneous massive corrosion of the surrounding tubing wall creates a relatively even cut with minimal distortion of the tubing, aiding subsequent fishing operations.

As used herein, a "jet cutter" is a type of cutter, generally run on wireline or coiled tubing, that uses the detonation of a shaped explosive charge to cut the surrounding tubing or casing wall. The cutting action leaves a relatively clean cut surface, although the explosive action tends to flare the cut ends.

As used herein, a "perforation tool" cuts small holes or slots in the tubulars. These are typically used to convert a designated region of casing to production use, the holes allowing ingress of oil. Such tools can also be used herein in the P&A process, to provide access to the annular space.

As used herein, an "expansion tool" is a downhole tool used to expand the diameter of a tubular. This is done either hydraulically, by applying mud pressure, or mechanically, by pulling the conical/tapered expansion tool, or by a rotating axial force.

As used herein a "rupture and expansion tool" is distinguished from an expansion tool, which leaves the casing intact, albeit bigger. Instead, this tool both ruptures and expands casings and tubings. Exemplary tools are being developed, and herein we have used prototypes that uses an energetic material (typically directional charges) that when ignited creates heat and large volume of gas in a short period of time. The material is designed to expand, rupture, and give annulus access in a controlled manner. Each device is designed for the particular tubular and casing in each well. The device can also be defined as "Tubular Expansion Rupture and Annular Access (TERAA)."

As used herein, "permanent plug" or "abandonment plug" refers to a plug that seals the well both laterally and vertically and is expected to provide long-term functionality. A modern requirement for a permanent well barrier is that it must include all annuli, extending to the full cross section of the well and seal both vertically and horizontally.

As used herein, "energetic material" refers to a class of materials with a high amount of stored chemical energy that can be released via exothermic heats of decomposition reactions. These materials include explosives, pyrotechnic compositions, propellants, and the like.

The term "self propagating" refers to the ability of the nano-thermite clusters to ignites adjacent clusters of material. In use, ignition in initiated by a point-heating of a small part of one cluster. Once started, the exothermic reaction sweeps through the remaining clusters.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

The following abbreviations are used herein:

| ABBREVIATION | TERM |
| --- | --- |
| Redox | reduction-oxidation reaction |
| MIC | metastable intermolecular composites |
| P&A | Ping and abandon-refers to setting permanent plugs |

DETAILED DESCRIPTION

Figure 1:
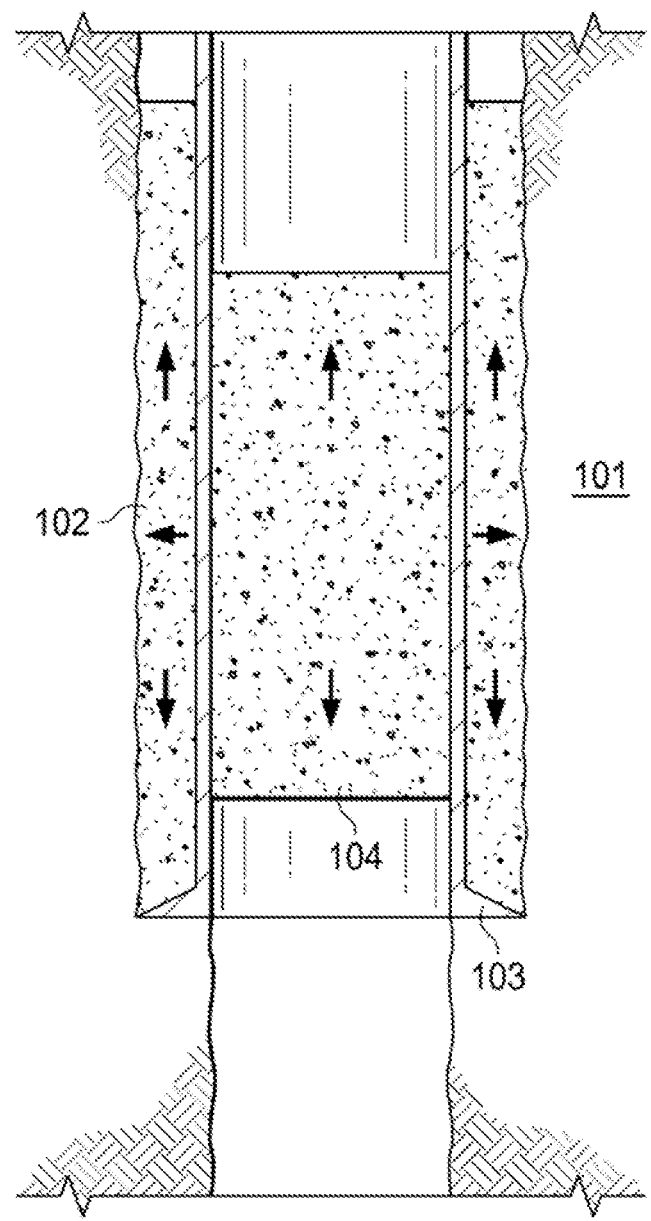
FIG. 1 provides a simple schematic of a basic plug. In this illustration, the cement plug is sealing vertically inside the casing and sealing both horizontally and vertically in the casing-formation annulus above the casing shoe.

The invention provides a novel plug composition and method for plugging a well to be abandoned.

The present methods include any of the following embodiments in any combination(s) of one or more thereof:

A composition for plugging a wellbore, said composition comprising molten metal from nano-thermite clusters of <500 nm average diameter admixed with molten metal from wellbore production tubing and casing.
A composition for plugging a wellbore, said composition comprising nano-thermite clusters of <500 nm average diameter plus expandable bismuth alloy pellets.
A composition or method as herein described, wherein said nano-thermite comprises an aluminum metal.
A composition or method as herein described, wherein said nano-thermite comprises $Fe_2O_3$, $Bi_2O_3$, $MoO_3$, or CuO.
A composition or method as herein described, wherein said nano-thermite comprises aluminum and $Bi_2O_3$.
A composition or method as herein described, wherein the nano-thermite clusters are coated with a low melt material, preferably expandable bismuth alloy.
A method for plugging a well comprising:
a) placing a heat resistant blocking device below and adjacent to a predetermined location for a permanent plug in a wellbore:
b) creating a void space above said blocking device:
c) introducing nano-thermite clusters of <500 nm average diameter into said void space in said wellbore;
d) igniting a thermite reaction in said nano-thermite using an ignition bailer in contact with at least one nano-thermite clusters, wherein said reaction is self-propagating from cluster to cluster;
e) removing said heater;
f) forming a permanent plug in said void space, wherein said permanent plug comprises admixed and cooled well metal and metal from said nano-thermite.
A method for plugging a well comprising:
a) placing a blocking device immediately below a predetermined location for a permanent plug in a wellbore;
b) creating a void space above said blocking device using a rupture and expansion tool to rupture and expand casing and production tubing;
c) placing a heat resistant base plate directly above and in contact with said blocking device and reaching reservoir walls;
d) introducing nano-thermite clusters of <500 nm average diameter into said void space in said wellbore and optionally metal pellets;
e) igniting a thermite reaction in said nano-thermite using an ignition bailer in contact with at least one nano-thermite cluster, wherein said reaction is self-propagating from cluster to cluster;
f) removing said ignition bailer;
g) melting said ruptured and expanded casing and production tubing and melting metal pellets in said nano-thermite; and,
h) forming a permanent plug in said void space, wherein said permanent plug comprises admixed and cooled molten casing and production tubing and molten metal from said nano-thermite and said optional metal pellets.

-continued

A method for plugging a well comprising:
a) placing a blocking device immediately below a predetermined location for a permanent plug in a wellbore;
b) creating a void space above said blocking device using a rupture and expansion tool to rupture and expand casing and production tubing;
c) placing a heat resistant base plate directly above and in contact with said blocking device and reaching reservoir walls;
d) introducing nano-thermite clusters of <500 nm average diameter into said void space;
e) introducing expandable bismuth alloy pellets info said void space;
f) igniting a thermite reaction in said nano-thermite, wherein said reaction is self-propagating from cluster to cluster;
g) melting said expandable bismuth alloy pellets; and,
h) cooling said melted expandable bismuth alloy pellets to form a permanent plug in said void space.
A method as herein described, wherein said void space is made with a rupture and expansion tool that ruptures and expands casing and production tubing in said wellbore.
A method as herein described, wherein said void space is made by milling <5 m of casing and production tubing.
A method as herein described, further comprising step g) pressure testing said permanent plug to ensure the seal is tight and h) repeating steps a-h) for one or more additional permanent plugs.
A method as herein described, wherein additional nano-thermite is added to said wellbore after removing the heater.
A method as herein described, wherein said nano-thermite comprises aluminum and a metal oxide.
A method as herein described, wherein said nano-thermite comprises aluminum and $Bi_2O_3$.
A method as herein described, wherein expandable bismuth alloy clusters are added to said void space before said igniting step.
A method or composition as herein described, wherein said expandable bismuth alloy clusters are <1 micrometer in average diameter.
A method or composition as herein described, wherein said expandable bismuth alloy clusters are <0.5 micrometer in average diameter.
A method as herein described, further comprising step i) repeating steps a-h for one or more additional permanent plugs.
A method as herein described, further comprising step i) pressure testing said permanent plug to ensure the seal is tight and j) repeating steps a-i for one or more additional permanent plugs.
A method as herein described, wherein additional nano-thermite is added to said wellbore after removing the heater.
A method or composition as herein described,, wherein said nano-thermite comprises aluminum and a metal oxide.
A method or composition as herein described, wherein said nano-thermite comprises aluminum and $Bi_2O_3$.
A method as herein described, wherein expandable bismuth alloy pellets are added to said void space before said igniting step
A method as herein described, wherein said ignition bailer having a meltable bottom and one or more ignition devices and wherein said ignition bailer also contains nano-thermite clusters.
A method as herein described, wherein said ignition device comprises thermite or nano-thermite.

FIG. 1 displays a simple schematic of a basic plug 104. A modern requirement for a permanent well barrier is that it must include all annuli 102, extending to the full cross section of the well and seal both vertically and horizontally. Typically, the procedure is to remove the tubing strings from the wellbore, then mill a window through all casing strings through which cement may be pumped into the annuli and against the exposed formation 101, making a "rock-to-rock" cement plug. A cement plug is sealing vertically inside the casing and sealing both horizontally and vertically in the casing-formation annulus above the casing shoe 103. Cement plugs are typically on the order of 50-100 m in length or more. Thus, the amount of milling required, the down-hole trips for each layer of casing, and the tons of swarf to be removed are significant. Another drawback is that highly viscous drilling fluid must be used during the milling operation to lift metal cuttings. This fluid with razor sharp metal cuttings can easily damage surface equipment when passing through it. As a consequence, plugging operations are time consuming and can be difficult to perform safely. Plus, the extra equipment and time needed add costs to the plugging and abandonment operations.

The present composition and methods overcomes one or more of these issues. A permanent plug in a soon-to-be abandoned well is created using a nano-thermite composition that heats and melts the adjacent metal tubing and casing. The nano-thermite components and melted metal form a plug that seals across the wellbore. The thermite reaction proceeds quickly and extensive and complicated equipment is not needed. Thus saving time and operational costs.

Nano-thermite is an especially useful material because it is small enough to be used in restricted wells, it requires less heat to initiate the thermite reduction-oxidation reaction, and the volume of the material can be tuned to each well being plugged. Additionally, the small size of particles increases the amount of surface area for the reaction, which in turn increases the reaction rate and produced heat. Thus, allowing the plug to be set quicker than one using conventional thermite.

In some embodiments, the nano-thermite is compressed and molded into clusters of various shapes and sizes. This allows for tuning the clusters to the needs of the well while retaining high energy reactions and self-propagation.

In wellbores that are undergoing P&A operations, one or more permanent plugs may be needed. Each plug can have the same specifications, per regulatory requirements, or different specifications. Further, the wellbore can have restricted tubing that must be considered in plugging the reservoir. The tune-ability of the nano-sized particles clusters makes nano-thermite the perfect choice for the various operations.

Figure 2C:
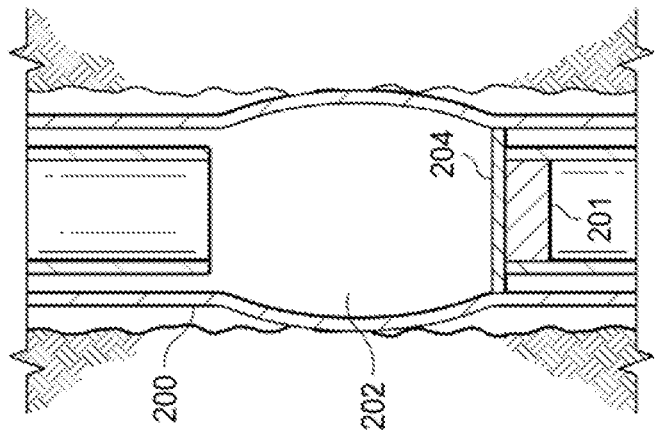
FIG. 2A-F. Displays wellbores after placement of a wide range setting plug (A); after the creation of a void space (B); placement of a heat resistant element (C); placement of nano-thermite material (D); placement of ignitor device at nano-thermite material (E); ignition of ignitor device and reaction propagated to the nano-thermite (F); and wellbore after the plug is formed (G).

To plug the wellbore at a predetermined location with nano-thermite, a wireline setting plug, basket or other blocking device is first placed below the area to be plugged. For wells with tubing 200 or restricted pipe, wide range of set bridge plugs can be used as a blocking device. As shown in FIG. 2A, the blocking device/plug 201 is located just below and adjacent to the predetermined location of the permanent plug. This blocking device 201 serves to provide a base for the cast-in-place nano-thermite generated plug to follow, preventing any pellets or molten material from falling downhole.

Figure 2B:
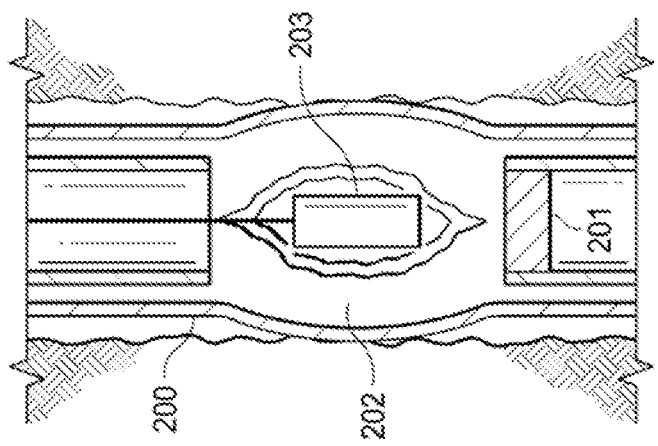
Figure 2A:
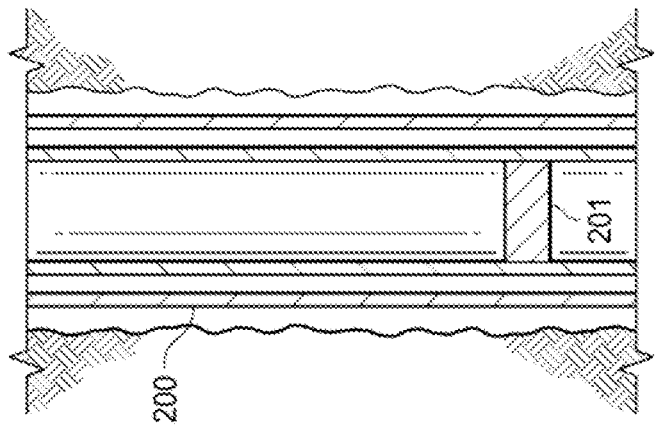

A void space 202 above the blocking device 201, FIG. 2B, is then created by removing a small section of casing and tubing with energetics, perforation tools, milling tools, cutting tools, and the like (collectively depicted as 203). This void space allows access to annulus, allowing a rock-to-rock plug. If a rupture and expansion tool is used, it will also fracture or pulverize any cement exterior to the casing, allowing it to fall downhole. Depending on dimensions of the tubulars, removal or rupture may not be necessary. The volume on nano-thermite required for the plug will determine if a removal or rupture is necessary.

The void space 202 allows for a larger volume of plug material to be placed by increasing the accessible width of the well. It also allows a rock-to-rock plug to be generated, consistent with many regulations. In some embodiments, additional nano-thermite can be added to the wellbore during the redox reaction to increase the length of the anticipated plug.

The void space 202 also creates access to the annulus to ensure that the casing metals are exposed to heat both internally and externally.

Once the void space is created, a heat resistant base plate 204 spanning the entire well bore width is placed above the original setting plug, at the bottom of the void space, FIG. 2C. If the original blocking device/plug 201 was heat resistant, this step can be avoided, but most existing blocking devices are not designed to handle termite temperatures, and a heat resistant base plate 204 will be needed. Any heat resistance material can be used, but ceramic or glass is preferred. The heat resistant material protects the setting plug from the heat of the thermite reaction. It also prevents nano-thermite material from dropping below the void space area.

Figure 2E:
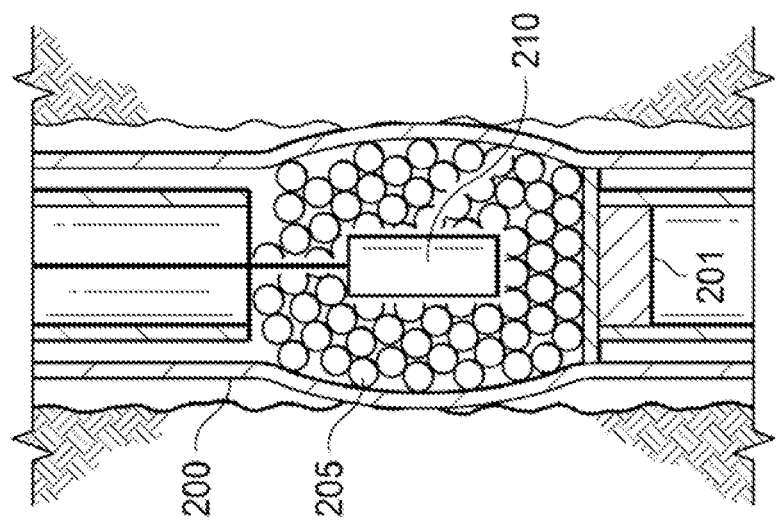
Figure 2D:
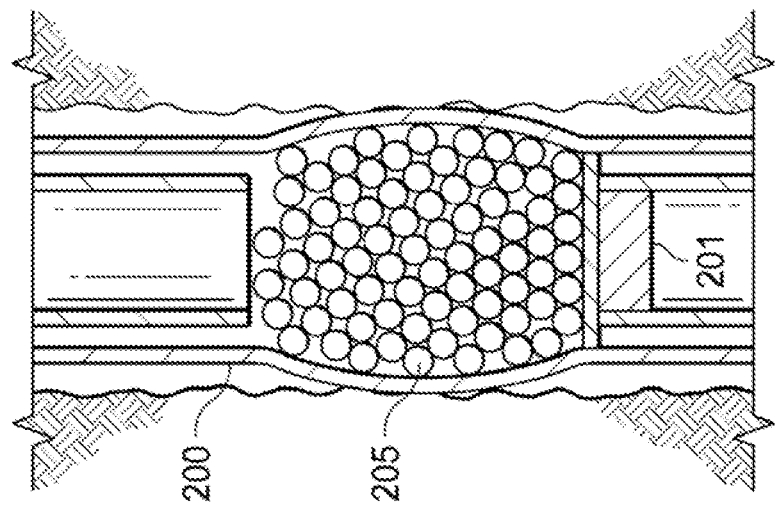

The void space 202 is then filled, or partially filled, with nano-thermite and any other optional plug material 205, FIG. 2D. The nano-thermite and other materials 205 can be placed by dropping with a dump bailer or dropping nano-thermite clusters and/or metal pellets from the surface.

Optional plug materials can include other types of metals to be melted by the nano-thermite. Ideally, low melt metals are preferred. However, due to the high temperature of the thermite reaction, which is expected to be around 3000° C., most metals, alloys, and eutectic metals can be used as optional plug material.

As already noted, expandable alloys, such as >50% bismuth alloys may be preferred because of their expansion on solidification, creating a very tight plug that fills all crevices, cracks and provides a very tight seal. Thus, such alloys can be dropped in with the nano-thermite, or can combine downhole with the nano-thermite and melted casing/tubulars to form such expandable alloys.

Figure 2F:
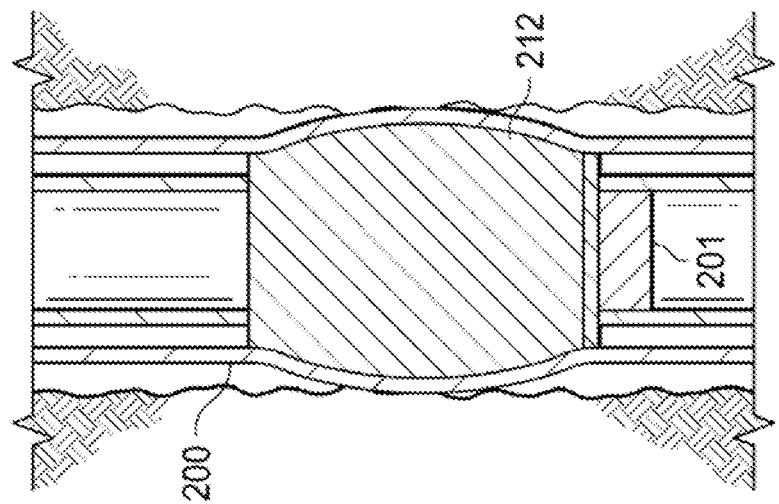

A heating device 210 is then introduced in the well and directly contacts the nano-thermite 205, initiating the nano-thermite reaction 211, FIG. 2E. Due to the efficient reactivity of the nano-thermite and large surface area, the reaction will proceed quickly and reach high enough temperatures to melt the metal in the nano-thermite material, which liquefies and easily flow into voids inside the wellbore and outside the casing, as shown in FIG. 2F. The flowing, melted metal can also contact and initiation the thermite reaction in unreacted nano-thermite.

Figure 2G:
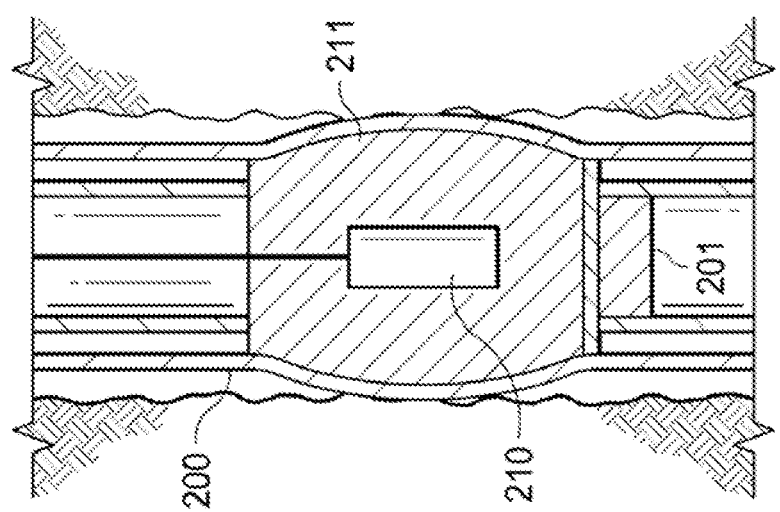

Once ignited, the heating device is preferably removed immediately to avoid deposition of materials onto its surface. Due to the reaction rate of the thermatic reaction, the metal plug 212 forms quickly, FIG. 2G.

In some embodiments, additional nano-thermite can be added during the redox reaction to maintain the high temperatures and allow a greater length of plug to be formed.

Figure 3:
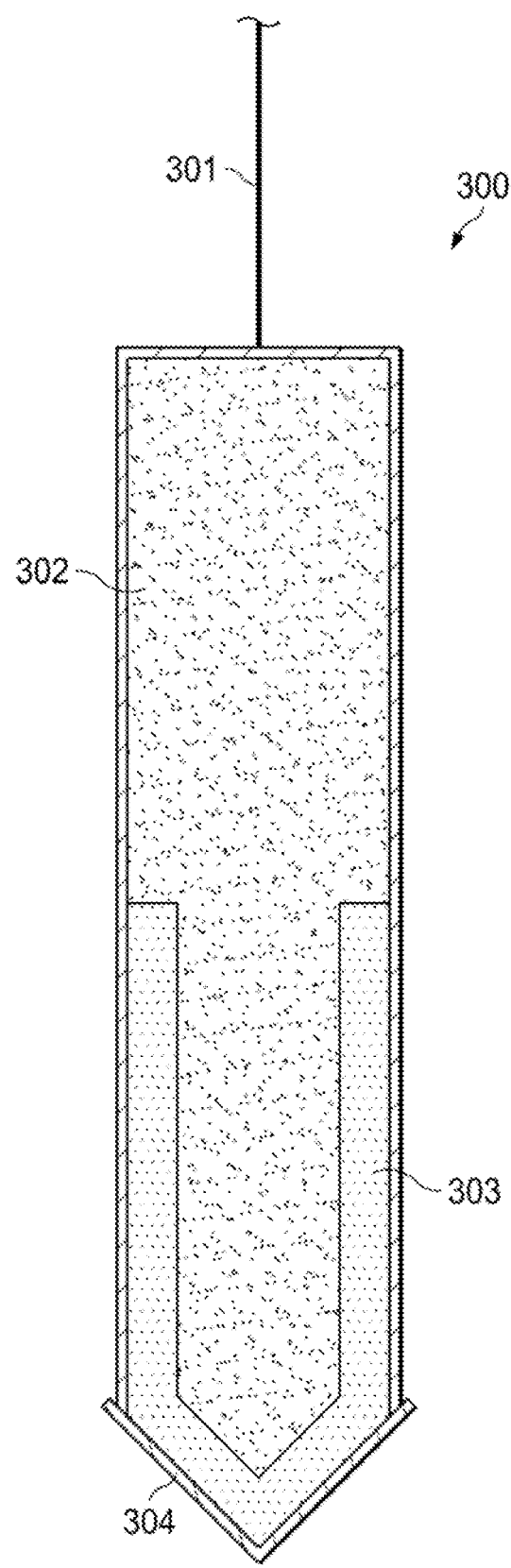
FIG. 3, displays an exemplary ignition bailer for use in the described methods.

FIG. 3 displays an exemplary ignition bailer 300 attached to a wireline 301 that can be used for ignition and for adding additional nano-thermite or optional thermite via a gravity feed. At the bottom of the bailer is a low temperature melt spud cone 304, low temperature melt base, and an ignitor mechanism 303. The ignitors 303 can span the diameter of the spud cone 304 and along at least a portion of the bailer. The ignition bailer is then filled with nano-thermite material or clusters or thermite 302 that is sufficient volume and heat content to reach ignition temperature of the clusters 205 in the well. If magnesium is used as the ignitor, this bailer will protect the magnesium and prevent spontaneous ignition and human contact.

Once in place, the ignitor will ignite the thermite reaction in the neighboring nano-thermite particles. The ignitor bailer will have thermite material ignitor to initiate the thermatic reaction in the nano-thermite clusters, and optional thermite 302. The reaction will then self-propagate to additional clusters (205, FIG. 2E), even in the presence of fluid.

The ignition bailer 300 can be a percussion type device that utilizes thermite or nano-thermite compositions as the ignitors mechanism 303. Thus, these ignitors will ignite the nano-thermite clusters while the bailer itself allows for the transfer of explosive energy of the nan-thermite reaction to the outer tubing to enable them to fail.

In some embodiments, additional metal is included in the ignition tool for high energy transfer from the tool itself to the nano-thermite clusters (e.g. FIG. 2, 205) placed in the well.

The heat generated by the redox reaction can easily melt adjacent metal tubings and casings. The explosive energy of the reaction may also contribute to local failure of the tubings, providing access to the annular space via ruptures. In some embodiments, additional materials are introduced with the nano-thermite material. Such materials can include expandable bismuth alloy pellets, as described herein. Any melted metal fluids will combine with the melted nano-thermite metals to form the plug.

After the thermite reaction burns out, the liquid metals will cool and form a seal that spans the entire wellbore, forming a permanent "cast-in-place" plug. Once the permanent plug is set, it can be tested to ensure a tight seal. Typically, positive and negative pressure tests are performed, as well as inflow tests, sonic or ultrasonic logs, but any known test can be used.

The present methods are exemplified with respect to the description using nano-thermite and metal in the wellbore casings and tubing. However, this is exemplary only, and the invention can be broadly applied to any metal-based permanent plug composition needed in a wellbore. The following examples are intended to be illustrative only, and not unduly limit the scope of the appended claims.

A skilled person will understand if it is desirable to set one, two or several permanent plugs, dependent on the desired operation and regulations.

A skilled person will understand if it is desirable to build one plug by layers. In some embodiments, nano-thermite clusters and a metal pellets will be introduced into the void space to create an initial plug layer, followed by repeated additions of nano-thermite and metal cluster to build additional layers for a single plug. The metal pellet composition can change such that the final plug has alternating layers of metal. This layering can be utilized for one, two or several permanent plugs.

The following references are incorporated by reference in their entirety.

US20150034317

COP 42399, U.S. Ser. No. 62/402,796

COP 42455, U.S. Ser. No. 62/402,821

U.S. Pat. No. 7,290,609 Subterranean well secondary plugging tool for repair of a first plug US20150368542 Heat sources and alloys for us in downhole applications U.S. Pat. No. 7,152,657 In-situ casting of well equipment US20060144591 Method and apparatus for repair of wells utilizing meltable repair materials and exothermic reactants as heating agents U.S. Pat. No. 6,828,531 Oil and gas well alloy squeezing method and apparatus U.S. Pat. No. 6,664,522 Method and apparatus for sealing multiple casings for oil and gas wells U.S. Pat. No. 6,474,414 Plug for tubulars

The invention claimed is:

1. A composition for plugging a wellbore, said composition comprising nano-thermite clusters of <500 nm average diameter plus expandable bismuth alloy pellets.

2. The composition of claim 1, wherein said nano-thermite comprises an aluminum metal.

3. The composition of claim 1, wherein said nano-thermite comprises $Fe_2O_3$, $Bi_2O_3$, $MoO_3$, or CuO.

4. The composition of claim 1, wherein said nano-thermite comprises aluminum and $Bi_2O_3$.

5. The composition of claim 1, wherein the nano-thermite clusters are coated with a thermoplastic or a fusible alloy.

6. The composition of claim 5, wherein said nano-thermite clusters are coated with a fusible alloy that comprises an expandable bismuth alloy.

* * * * *